United States Patent [19]

Davidson

[11] 3,951,821

[45] Apr. 20, 1976

[54] DISINTEGRATING AGENT FOR TABLETS

[75] Inventor: William G. Davidson, Carmel, Ind.

[73] Assignee: The Dow Chemical Company, Midland, Mich.

[22] Filed: Sept. 20, 1974

[21] Appl. No.: 508,025

Related U.S. Application Data

[63] Continuation of Ser. No. 271,829, July 14, 1972, abandoned.

[52] U.S. Cl. ................................ 252/1; 424/15; 424/362; 252/134; 252/363.5
[51] Int. Cl.² ............................................ C09K 3/00
[58] Field of Search .................. 424/15, 361, 362; 252/1

[56] References Cited
UNITED STATES PATENTS

| | | | |
|---|---|---|---|
| R27,679 | 6/1973 | Bentholm et al. | 424/362 |
| 3,181,998 | 5/1965 | Kanig | 424/361 |
| 3,622,677 | 11/1971 | Short | 424/321 |

Primary Examiner—Benjamin R. Padgett
Assistant Examiner—Josephine Lloyd
Attorney, Agent, or Firm—Maynard R. Johnson

[57] ABSTRACT

Disintegration of tablets is improved by the incorporation therein of a plurality of small tubules. The tubules can be prepared by subdivision of hollow fibers such as cellulose or cellulose acetate hollow fibers having inside diameters on the order of 50–300 microns into segments 100–1000 microns in length. Tablets and methods for their preparation are disclosed.

5 Claims, No Drawings

DISINTEGRATING AGENT FOR TABLETS

CROSS-REFERENCE TO RELATED APPLICATION

This is a continuation of application Serial No. 271,829 filed July 14, 1972 now abandoned.

BACKGROUND OF THE INVENTION

A number of materials have been used to enhance or control disintegration of tablets on exposure to a liquid medium. For example, U.S. Pat. No. 3,383,283 discloses stearic acid-talc mixtures; U.S. Pat. No. 3,629,393 discloses water-swellable granules; and U.S. Pat. No. 3,435,110 describes a collagen matrix to enhance disintegration.

SUMMARY OF THE INVENTION

The present invention provides a novel tablet disintegrant for tablets in the form of small tubular particles incorporated within the tablet structure. The tubular particles are fabricated of a material which is compatible with the other ingredients of the tablet, and which has character strength to maintain the hollow, tubular structure of the particles without complete occlusion through the compression of the tablet. Incorporation of such tubular segments in a tablet provides a tablet with a plurality of small open-ended chambers (internally of the segments) and a plurality of openings in the face of the tablet.

The term "tablet" is employed herein in its usual sense to refer to a compressed or molded mass of solid material comprising an active ingredient such as a drug, a soap, a disinfectant, a fertilizer, an insecticide, a dye, a foodstuff, etc., which active ingredient is intended in use to be ultimately dispersed or dissolved in a liquid such as water, gastric fluid, oil, emulsions, chemical solutions, etc. For the purposes of the invention, the shape and size of a tablet can vary considerably from the conventional rounded disk shape or capsule shape associated with pharmaceutical tablets, to irregularly shaped masses, bars, pellets, balls, beads, cakes, or the like.

The tubular segments of the invention are hereinafter referred to as "tubules" to reflect both their hollow, open-ended tubular character, and their small size in relation to the size of the ultimate tablet. The tubules are generally more or less cylindrical in shape. Their cross-sectional dimensions are most conveniently expressed in terms of inside diameter (I.D.), it being understood that the tubules can have circular, ellipsoidal, oval, polygonal or irregular in cross-section and that inside diameter is employed as a convenient expression of internal area. The length of the tubules is likewise conveniently expressed as the axial length of a cylindrical segment, it being understood that the tubules may also be curved or bent, and that the ends thereof need not be in a plane normal to an axis, or even precisely planar. The wall thickness of the tubules is conveniently expressed in terms of outside diameter.

In general, the tubules have an inside diameter on the order of from about 5, to about 10, to about 25, to about 100, to about 1000 microns. Tubule length will generally be from about 50 microns to 2 to 3 millimeters. The wall thickness should be sufficient to maintain the tubular form of the tubules in a compressed tablet, and is preferably thin enough to be readily water-permeable. The tubules can have outside diameters ranging from about 10 to about 50 microns to about 300 to about 1100 microns, preferably having an outside diameter of about 5 to 10 to 50 to about 300 microns greater than the inside diameter. Axial length can be as low as 0.5 microns, but is preferably at least as great as the inside diameter, and is preferably about 100–1000 microns.

In general, the tubules are fabricated of a synthetic organic polymeric material having a density less than 1 gram per cubic centimeter. In quantity, such organic polymeric tubules will generally have a bulk density on the order of 0.1 to about 0.6 grams per cubic centimeter, or from about 1000 to about 45,000 tubules per cubic centimeter.

Preparation of the Tubules

The tubule disintegrating agents of the invention can be conveniently prepared by cutting or otherwise subdividing hollow fibers into segments of the desired length. The hollow fibers of a desired material, dimensions and shape can in turn be prepared by well-known procedures. For example, hollow fibers can be prepared by coating a filamentous core, and thereafter dissolving the core material, as taught by Snelling, U.S. Pat. No. 1,713,679, by drawing a relatively large tube, or by extrusion or melt spinning, as disclosed, for example, in U.S. Pat. Nos. 3,616,928; 3,536,611; 3,492,698; 3,228,456; 3,494,121 and 3,423,491. Hollow fibers of various types are also commercially available for use in permeation separatory devices such as hemodialysis or desalinization devices or heat exchange devices. These commercially available hollow fibers can be segmented to form tubules. The tubules employed in the present invention are much shorter in length than the hollow fibers employed in applications such as reverse osmosis devices. Accordingly, broken or imperfect fibers prepared for other uses can be segmented for use in the present invention. Also, the manufacture of hollow fibers for preparation of tubules can be greatly simplified, since the length of the hollow fiber starting material is much less critical.

Disintegratable Tablets

The invention provides tablets containing the tubules as disintegrating agents. The tubules are incorporated in a tablet in an amount effective to enhance disintegration of the tablet, and can be employed over a wide range of concentrations, from about 0.1 to about 90 or more percent by weight of the ultimate tablet. In addition to their function as disintegrating agents, the tubules can be dyed a color which contrasts with the other tablet ingredients, to aid in tablet identification, and the longer tubules, e.g. 500–3000 microns in length, add strength to the tablet structure.

When a tablet of the invention is contacted with a liquid, the tubules in the tablet face can draw liquid rapidly into the tablet by capillary action. Within the tablet local dissolution of ingredients can occur at the internal ends of tubules, thus providing additional channels for the liquid to move from tubule to tubule within the tablet. The increase in disintegration rate is thus dependent in part upon factors having to do with capillary attraction, such as wettability of the tubules, dimensions of tubules, and surface tension. When the tubules are fabricated from a material which is permeable to the liquid, the tubule walls can serve as dialysis membranes through which the liquid can migrate. In such an embodiment, the disintegration rate is also influenced by factors having to do with osmotic pressure, such as tubule wall permeability, electrolyte concentrations, pressure and the like. The tubules can also be fabricated of materials such as water-swellable polymers which imbibe or react with the liquid and swell, in which case enhancement of disintegration is further related to mechanical disruptive forces generated in such swelling. Additionally, the tubule material may itself be soluble in the liquid, in which case additional factors contribute to disintegration.

It will thus be apparent that the disintegration mechanisms involved in the invention can be quite complex from a theoretical standpoint. Accordingly, particular theories or combination of theories should not be considered as controlling. It will also be apparent that the invention provides a high degree to practical flexibility for adaptation of the invention to a variety of environments.

Quantity of Tubules

Due to their small size, the disintegrant tubules of the invention are most conveniently measured in bulk by weight or by volume. In most applications it is desirable to measure the ingredients and the final tablets in terms of weight. Accordingly, quantities of tubules are also most conveniently expressed in terms of weight. It is understood that for a given type of tubule, weight is also an indication of volume, and of number of tubules.

In the preparation of tablets of the invention, the material to be formed into tablets is mixed together in accordance with conventional procedures for formulating and mixing a solid mass to be tabletted. A plurality of tubules is mixed with the other ingredients prior to tablet formation, and the mass is then compressed into tablets (or granules) of the desired size and shape, according to conventional techniques. Sufficient tubules should be employed to enhance the disintegration of the final tablet or granule. The exact quantity of tubules to be employed in a given case can vary considerably depending upon such factors as the tablet ingredients, liquid intended for disintegration in ultimate use, the manner in which the tablets are formed, size of tablets, the particular type of tubules employed, and disintegration rate desired. The quantity of tubules to be employed in a given case can be readily selected by determining disintegration rates for tablets or granulations prepared with different quantities of tubules using conventional equipment and procedures.

In general, excellent results have been obtained with tablet formulations in which the tubules amount to from about 0.1 to about 1 to about 20 percent by weight of the tablet formulation. The tubules can be employed in higher amounts, such as from 1 to 50 to 85 to 90 percent by weight of the total tablet. In most instances, however, an amount of tubules in excess of 10 to 15 percent of the tablet weight provides little additional increase in disintegration rate, while the active ingredient concentration as a percentage of tablet weight correspondingly is reduced. For most pharmaceutical tablets and granulations the tubules preferably comprise from about 1 to about 10 percent by weight of the tablet or granule, and outstanding results can be obtained with amounts of about 5 to 7 percent. Depending upon the size of the ultimate tablet and the size of tubules employed the absolute number of tubules per tablet can be as low as one in the case of "micro" tablets or "beadlets" more generally regarded as granules, to hundreds, thousands or millions, or more, individual tubules per tablet.

Preparation of Tablets

In a convenient tabletting procedure, the active ingredient or ingredients and any other ingredients (other than the tubules) such as binders, stabilizers, flavors, antioxidants, lubricants, delayed release coatings, running powder, dyes, buffers, etc. are intimately mixed together to form a mass ready for compression or molding into tablets. The ingredients may be granulated by conventional "wet" or "dry" granulation techniques, for example, or portions of the ingredients may be coated according to known procedures to provide for delayed or timed dissolution of the coated ingredients. The disintegrant tubules are then mixed with the dry mixture of ingredients. If a wet granulation procedure is employed, or when a liquid coating is applied, the resulting wet granulate or coated material is preferably dried prior to addition of the tubules although the tubules can be employed in wet granulation techniques as well. The resulting mixture is then compressed into tablets.

The exact type of tubule to be employed depends on the desired use of the ultimate tablet. For most applications with tablets for disintegration in water, tubules are preferably fabricated of a material such as, carboxy methyl cellulose, ethyl cellulose, cellulose, cellulose acetate, gelatin or hydroxypropyl methyl cellulose; and have an inside diameter of about 30 to about 300 microns, a wall thickness of about 5 to about 50 microns and a length of about 100 to 700 microns.

The tablets can be coated according to known procedures for spray coating or press coating, for example, or they can be left uncoated, as may be desired. Coating can be employed advantageously to control disintegration time. In such embodiments, the tubule disintegrants ensure positive rapid disintegration of the tablet once the coating material has been removed.

DESCRIPTION OF PREFERRED EMBODIMENTS

The following examples illustrate the invention:

EXAMPLE 1

Hollow cellulose acetate dialysis fibers having an inside diameter of 200 microns and a wall thickness of about 50 microns are cut into roughly cylindrical segments approximately 0.5 – 1 millimeter in length. 50 Parts by weight of the tubular fiber segments are mixed thoroughly with 700 parts by weight of crystalline aspirin. The mixture is compressed into tablets using a 0.5 inch standard curvature punch and die on a Manesty F-3 tablet machine. The tablets are compressed to a tablet hardness, of about 8–10 Strong-Cobb-Arner Units (corresponding to about 2000–3000 psi compression pressure). Disintegration time in 0.1 normal hydrochloric acid is determined according to U.S.P. procedures and found to be less than 2 minutes. Tablets of similar hardness compressed from the same crystalline aspirin alone have a disintegration time in excess of two hours.

EXAMPLE 2

In a similar procedure, tablets are prepared using 700 parts by weight of the same crystalline aspirin, with 50 or 30 parts by weight of the tubular segments, or with 50 parts by weight of a microcrystalline cellulose disintegrant. Two drops of aqueous methylene blue dye are placed on a tablet of each type and the tablets are observed. The tablets containing the hollow tubule disintegrant are found to fracture and disintegrate into moist segments within about one to two minutes. The tablet containing the solid cellulose disintegrant is observed to absorb the dye solution while retaining its physical integrity.

EXAMPLE 3

750 Parts by weight of a rifampin tablet granulation containing 600 parts by weight of rifampin and 146 parts by weight of starch and 4 parts by weight of magnesium stearate is mixed with 50 parts by weight of cellulose acetate tubules prepared as described in Example 1. Tablets weighing 750 milligrams are compressed to equal hardness from this mixture, and from the granulation alone. The tablets containing the tubules are found to disintegrate in about 5 minutes in 0.1 normal hydrochloric acid with corresponding dissolution of the active ingredient, while the corresponding tablets without the tubule disintegrant are found to remain intact after 30 minutes.

Similar results are obtained with cellulose tubules of similar dimensions.

EXAMPLE 4

90 Grams of sodium bisulfite are mixed with 15 grams of ethyl cellulose as a solution in ethanol, (about 5 percent by weight) and the wet mass is passed through a screen having 8 meshes to the inch. The wet granulate is dried at room temperature, then passed through a screen having 12 meshes to the inch. The dry granulation is then spray coated with shellac applied in alcohol solution.

40 Grams of sodium iodide are mixed with 15 grams of ethyl cellulose dissolved in sufficient ethanol to give a wet granulation, and the wet mixture is wet-screened through a screen having 8 meshes to the inch, then dried.

The two foregoing granulates are mixed thoroughly with 20 grams of solid 2,2-dibromo-3-nitrilopropionamide and 25 grams of starch. The resulting dry mixture is then blended with a 20 gram quantity of hollow tubules of hydroxypropyl ethyl cellulose having an average inside diameter of 225 microns and an average length of 0.3 – 0.8 millimeters. The mixture is compressed into tablets weighing about 10 grams each. The tablets are adapted for use as disinfectants of aqueous systems such as water closets, humidifier tanks, wading pools and the like. In use the tablet disintegrates to provide an initial release of the 2,2-dibromo-3-nitrilopropionamide disinfectant and sodium iodide synergist, followed by a later gradual release of sodium bisulfite which detoxifies the disinfectant to permit safe discharge of the disinfected water.

EXAMPLE 5

A series of different hollow fibers of cellulose acetate containing varying amounts of a tetramethyl sulfone plasticizer, and of various sizes, are cut into substantially cylindrical segments. The resulting tubules, substantially all of which are between 500 and 2000 microns in length, are then evaluated for agglomeration on a scale of 1 to 5, with 1 representing free flowing tubules with substantially no agglomeration and 5 representing clumping. The fibers in each series are examined microscopically dry, after wetting with water; and after redrying. The observations are set out below, the O.D. measurements being in microns. With the exception of series 8, the inside diameter is about 200 microns, series 8 being about 50–60 microns I.D.

| Series | Agglomeration | Dry O.D. | Wet O.D. | Redried O.D. |
|---|---|---|---|---|
| 1 | 1 | 210 | 290–300 | 220 |
| 2 | 3 | 250 | 260–265 | 230–240 |
| 3 | 2 | 240 | 250 | 160 |
| 4 | 3 | 220 | 260–265 | 160–165 |
| 5 | 4 | 260–275 | 280 | 270–280 |
| 6 | 3 | 260 | 265–270 | 170 |
| 7 | 5 | 240–250 | 260–270 | 160–170 |
| 8 | 5 | 70 | 70 | 65 |
| 9 | 1 | 210–220 | 250–260 | 190–200 |

During wetting, water is observed to flow into the tubules, indicating capillary action. With the exception of tubule series 8, significant expansion of tubules is observed indicating that both capillary attraction of water and mechanical disruption of tablet structure will take place. On redrying, shrinkage is generally uniform, the tubules retaining the same shape throughout wetting and drying.

EXAMPLE 6

Tubules from series 9 of Example 5 are screened to give a batch of tubules, substantially all of which are between 60 and 700 microns in length. Two batches of tubules are separately dyed with about two drops of aqueous F. D. & C. Blue No. 1 to about 5 cc. of tubules. One batch is dried in air at room temperature, the second is oven dried at about 45°C. The resulting blue tubules are mixed with aspirin and tablets are prepared following the procedure described in Example 1. Visually the tablets have a distinctive blue and white speckled or mottled appearance. Under microscopic examination, tubules lying along the faces of the tablet are seen to be flattened. Tubules at the face, but extending axially into the tablet are seen to retain a substantially circular cross section, presenting a large number of relatively uniform capillary-sized openings in the tablet face.

Disintegration studies with these tablets show dramatic reductions in disintegration time, with results similar to those set out in Examples 1 and 2.

EXAMPLE 7

A tablet granulation is prepared containing 600 parts rifampin, 150 parts starch, 40 parts calcium carbonate, 8 parts magnesium stearate and 2 parts sodium lauryl sulfate, 400 parts by weight of the granulation is mixed with 25 parts by weight of tubules. The tubules employed are of regenerated cellulose plasticized with glycerine, the glycerine also serving as a wetting agent to enhance capillarity. The tubules have an I.D. of about 200 microns, an O.D. of 225 microns and substantially all (over 95 percent) are between 60 and 700 microns in length.

One lot of 425 milligram tablets is compressed from the resulting tubule granulation to a hardness of 10 Strong-Cobb-Arner units. A similar lot of 400 milligram control tablets are prepared from the granulation alone. The tablets containing 6.25 percent by weight of tubules have a disintegration time in artificial gastric juice of 3–5.3 minutes, as compared to 43–55 minutes for the control tablets.

The "tubule tablets" and control tablets are orally administered to separate groups of dogs, five dogs per group. Blood samples are withdrawn at timed intervals and assayed for serum drug levels. The average serum levels of rifampin in the control group at 0,1,2,4,6 and 24 hours after dosing, are 0,0.4,1.2,1.2,1.2, and 0.5 micrograms per milliliter. The blood levels in the test group at the same time periods are 0, 5.1, 7.4, 7.3, 7.0 and 1.9 micrograms per milliliter of serum, indicating that much higher blood levels of the active ingredient are obtained by the use of the tubule disintegrant.

EXAMPLE 8

A mixture of 200 parts (by weight) quinidine sulfate, 35 parts starch, 2.5 parts magnesium stearate and 1.25 parts lubricant (Sterotex) is granulated. Tablets are compressed to a hardness of about 5–7 Strong-Cobb-Arner units, sized to contain 200 milligrams quinidine sulfate per tablet. One lot is from the granulation alone and one lot from a mixture containing 7 percent by weight regenerated cellulose tubules plasticized with glycerine, 200 microns I.D., 60–700 microns long, 225 microns O.D. The tablets containing the tubule disintegrant have a disintegration time of about 3 minutes, as compared to 17 minutes for tablets without the tubules.

I claim:

1. In a compressed tablet comprising an active ingredient and an effective amount of a disintegrating agent to facilitate disintegration of the tablet in contact with a liquid, the improvement wherein the disintegrating agent comprises a tubule, said tubule having an internal cross-sectional area corresponding to an inside diameter of from about 5 microns to about 2,000 microns, and a length corresponding to an axial length of from about 0.5 micron to about 3 millimeters, said tubule being wettable by the liquid.

2. The tablet of claim 1 wherein the tablet contains a plurality of said tubules.

3. The tablet of claim 2 wherein the tubules are of a liquid permeable material.

4. The tablet of claim 2 wherein the tubules are of a material adapted to swell on contact with the liquid.

5. The tablet of claim 2 wherein the tubules are of a material selected from the group consisting of ethyl cellulose, cellulose acetate, gelatin, cellulose, hydroxypropyl methyl cellulose.

* * * * *